(12) United States Patent
Tai et al.

(10) Patent No.: US 10,736,537 B2
(45) Date of Patent: Aug. 11, 2020

(54) ELECTRICAL IMPEDANCE SPECTROSCOPY MEASUREMENT BASED ON CONCENTRIC BIPOLAR MICROELECTRODE SENSOR

(71) Applicants: California Institute of Technology, Pasadena, CA (US); University of California Los Angeles, Los Angeles, CA (US); University of Southern California, Los Angeles, CA (US)

(72) Inventors: Yu-Chong Tai, Pasadena, CA (US); Tzung Hsiai, Santa Monica, CA (US); Yu Zhao, Shenhen (CN); Xiaoxiao Zhang, Los Angeles, CA (US); Fei Yu, Chatsworth, CA (US)

(73) Assignees: CALIFORNIA INSTITUTE OF TECHNOLOGY, Pasadena, CA (US); UNIVERSITY OF CALIFORNIA LOS ANGELES, Los Angeles, CA (US); UNIVERSITY OF SOUTHERN CALIFORNIA, Los Angeles, CA (US)

( * ) Notice: Subject to any disclaimer, the term of this patent is extended or adjusted under 35 U.S.C. 154(b) by 1261 days.

(21) Appl. No.: 14/981,089

(22) Filed: Dec. 28, 2015

(65) Prior Publication Data
US 2017/0100054 A1    Apr. 13, 2017

Related U.S. Application Data

(60) Provisional application No. 62/240,291, filed on Oct. 12, 2015.

(51) Int. Cl.
*A61B 5/053*    (2006.01)
*A61B 5/00*    (2006.01)

(52) U.S. Cl.
CPC .......... *A61B 5/0538* (2013.01); *A61B 5/6853* (2013.01)

(58) Field of Classification Search
CPC ..... A61B 5/0538; A61B 5/6853; A61B 5/053; A61B 2018/0022; A61B 2018/0025; A61B 2018/00285
See application file for complete search history.

(56) References Cited

U.S. PATENT DOCUMENTS

2005/0112544 A1* 5/2005 Xu .................. C12M 23/12
                                                435/4
2012/0061257 A1* 3/2012 Yu .................. A61B 5/02007
                                                205/792

(Continued)

*Primary Examiner* — Lee S Cohen
*Assistant Examiner* — Erin M Cardinal
(74) *Attorney, Agent, or Firm* — Kilpatrick Townsend & Stockton LLP

(57) ABSTRACT

A portion of a concentric bipolar microelectrode sensor is attached to an inflatable balloon of a catheter. Another portion of the concentric bipolar microelectrode sensor is also attached to a body of the catheter. The inflatable balloon is guided to become in proximity of a tissue. The inflatable balloon is then inflated. The inflation increases the likelihood of contact between microelectrodes of the concentric bipolar microelectrode sensor with the tissue. A voltage is supplied to the microelectrodes. The tissue's impedance is accordingly measured over a frequency range. A disease of the tissue, such as a lesion, is diagnosed based on the measured impedance.

20 Claims, 11 Drawing Sheets

(56) References Cited

U.S. PATENT DOCUMENTS

2013/0150693 A1\* 6/2013 D'Angelo .............. A61B 5/036
600/373
2013/0274562 A1\* 10/2013 Ghaffari ............. A61B 18/1492
600/301

\* cited by examiner

ELECTRICAL IMPEDANCE SPECTROSCOPY MEASUREMENT BASED ON CONCENTRIC BIPOLAR MICROELECTRODE SENSOR

CROSS-REFERENCES TO RELATED APPLICATIONS

This application claims the benefit of U.S. Provisional Application No. 62/240,291, filed Oct. 12, 2015, the contents of which are hereby incorporated in their entireties for all purposes.

STATEMENT AS TO RIGHTS TO INVENTIONS MADE UNDER FEDERALLY SPONSORED RESEARCH AND DEVELOPMENT

This invention was made with government support under Grant No. HL111437 and Grant No. HL083015 awarded by the National Institutes of Health. The government has certain rights in the invention.

BACKGROUND OF THE INVENTION

Electrical Impedance Spectroscopy (EIS) measures the electrical impedance of a substance as a function of the frequency of an applied electrical current. An application of the EIS includes measuring the electrical impedance of biological tissues. Generally, a biological tissue exhibits electrical impedance that varies with frequency. The biological tissue contains components with both resistive and capacitive properties resulting in a complex electrical impedance. The magnitude and phase of the electrical impedance and the dependence of the electrical impedance on frequency are functions of the tissue's composition. Measuring the electrical impedance across a range of frequencies will generate a spectrum that is characteristic of the biological tissue. Changes in the impedance spectrum can be related to changes in the underlying nature of the biological tissue.

EIS measurements are relevant to many medical applications, such as plaque diagnostics in an artery or in other blood vessels. For example, EIS measurements can help diagnose Oxidized low-density lipoprotein (OxLDL) lesions on an intima of an artery. Generally, the accuracy of an EIS-based medical application depends on the accuracy of the EIS measurements. As such, accurately measuring the impedance of a biological tissue is of utmost importance in the EIS-based medical application.

BRIEF SUMMARY OF THE INVENTION

Generally described is an electrical impedance sensor for electrical impedance spectroscopy (EIS) measurement. In an example, the sensor is a component of an EIS measurement system for diagnosing a lesion of a tissue. The sensor includes an outer electrode and an inner electrode, each disposed in a flat, circular ring. The outer electrode substantially surrounds the inner electrode such that the two electrodes are disposed in a concentric configuration. The sensor also includes a pair of pads to attach the electrodes to an inflatable balloon of a catheter. The pads are disposed on opposite sides of the concentric electrodes. A biocompatible glue is usable to affix the pads to an outer surface of the inflatable balloon. The sensor also includes a pair of electrical contact surfaces. For instance, the electrical contact surfaces include conductive pads. A conductive epoxy is used to affix the electrical contact surfaces to a body of the catheter. In addition, the sensor includes a pair of ribbon cables connecting the two electrodes to the electrical contact surfaces. One of the ribbon cables connects the inner electrode to one of the electrical contact surfaces, while the other ribbon cable connects the outer electrode to the other electrical contact surface. Each of the ribbon cables has a serpentine length, thereby configured to extend and retract with an inflation and deflation of the inflatable balloon. When attached to the catheter, the sensor enables accurate EIS measurements. In an example, the catheter is guided to a location proximate to biological tissue. The inflatable balloon is inflated to contact the biological tissue. Thus, the sensor also becomes in contact with the tissue. Voltage is applied through the electrodes, and the tissue's impedance is thereby more accurately measured.

In an example, conductive and non-conductive materials are used to manufacture the electrical impedance sensor. The conductive material includes, for instance, gold or platinum. The non-conductive material includes, for instance, parylene. The manufacturing process includes deposition of the materials on a substrate, etching and lithography applied to the materials, and removal of the sensor from the substrate. The resulting sensor can be attached to the catheter such that the two electrodes are affixed to the surface location of the inflatable balloon and the electrical contact surfaces are affixed to the body the catheter. A coaxial cable running along a portion of the catheter is connected to the electrical contact surfaces. The coaxial cable provides the voltage to the electrical impedance sensor from a voltage source.

Generally also described is an electrical impedance apparatus. In an example, the apparatus includes the catheter having the inflatable balloon and the electrical impedance sensor. The two components are attached as described herein above. In this example, the coaxial cable is also connected to an analysis system. The analysis system compares the measured impedance to impedance models or impedance baselines. The comparison identifies whether a lesion of the tissue exists.

In an example, the apparatus is manufactured by fabricating the inflatable balloon and the electrical impedance sensor, attaching the two components, and connecting the coaxial cable. The fabrication of the inflatable balloon includes multiple operations. These operations include, for instance, forming a droplet of photoresist (PR) at an end of the catheter, coating a portion of the droplet with silicone, opening an uncoated portion of the droplet, removing the PR to create an opening corresponding to the uncoated portion of the droplet, and sealing the opening with silicone.

Generally also described is a method of performing electrical impedance spectroscopy (EIS) measurement to diagnose a lesion of a tissue. The method includes inflating the inflatable balloon when the balloon is in proximity of the tissue. The method also includes applying a voltage across the outer electrode and inner electrode of the electrical impedance sensor. The method further includes measuring an impedance of the tissue based on the voltage. The method yet includes detecting the lesion based on the impedance.

DETAILED DESCRIPTION OF THE INVENTION

Figure 1:
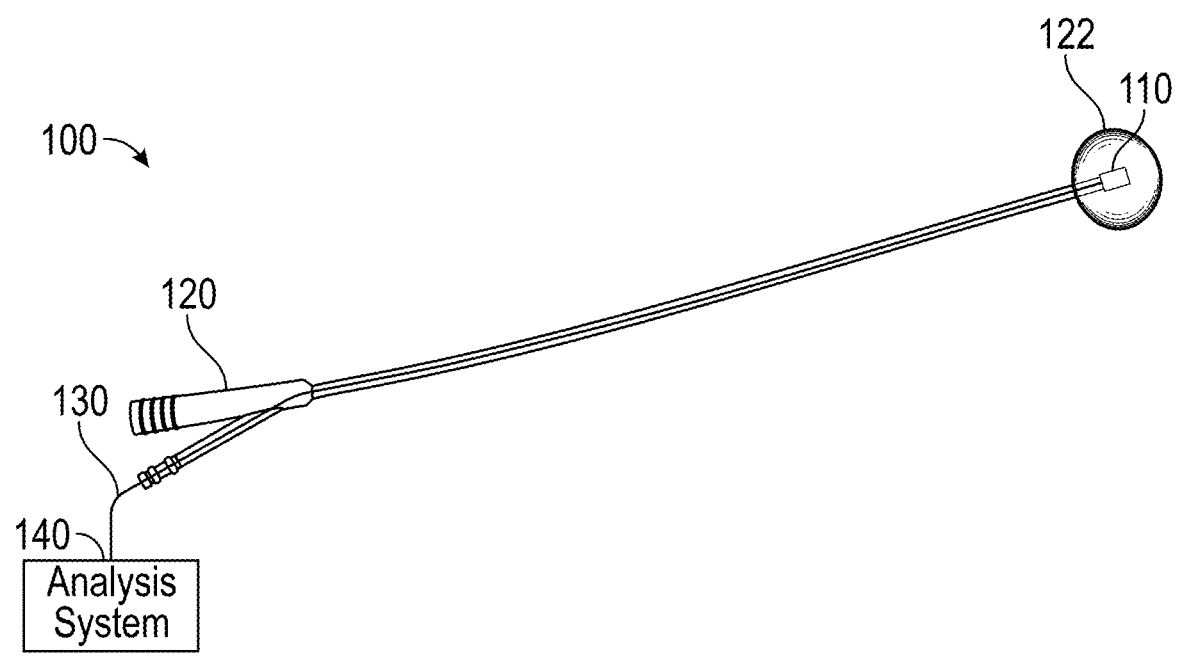
FIG. 1 illustrates an example electrical impedance spectroscopy (EIS) system for diagnosing a lesion of a tissue, in accordance with an embodiment.

Specific details of various exemplary embodiments of the present invention are set forth in the following description and are illustrated in the figures. Certain well-known technology details, such as methods, apparatus, or systems that would be known by one of ordinary skill, are not set forth in the following description or in the figures to avoid unnecessarily obscuring the various examples. Those of ordinary skill in the relevant art will understand that they can practice other examples of the disclosed subject matter without departing from the scope and spirit of the present invention.

Embodiments for an electrical impedance sensor and an electrical impedance apparatus for electrical impedance spectroscopy (EIS) measurement are described. Embodiments for methods of manufacturing such a sensor and apparatus are also described. In addition, embodiments for a method of performing EIS measurement to diagnose a lesion of a tissue is described. The embodiments improve the accuracy of certain EIS-based medical applications. For ease of reference, the electrical impedance sensor is also referred to as an EIS sensor in the present disclosure.

An example EIS-based medical application includes detection and diagnosis of the non-obstructive and pro-inflammatory atherosclerotic lesions in human arteries during catheterization. Biological tissues store charges. Electric impedance (Z) develops as a function of frequency in response to an applied alternating current (AC). Accordingly, atherosclerotic lesions can display distinct electrochemical properties. Active lipids and macrophages cause distinct electrochemical properties in the vessel wall that can be measured by EIS. Distinct electrochemical properties of oxidized low density lipoprotein (oxLDL) and foam cell infiltrated in the subendothelial layer at lesion sites can be measured in terms of the EIS using concentric bi-polar electrodes as described herein. Concentric bipolar microelectrodes can accordingly be used to measure electrochemical impedance in regions of pro-inflammatory states with high spatial resolution. Concentric electrodes can provide constant and symmetric displacement between working and counter electrodes. Moreover, concentric configuration can allow for EIS measurement independent of the surrounding solutions or blood and the orientation of the tissues. Because of the micro-scale of the concentric electrodes, the impedance measurement is mainly sensitive to the electrochemical properties of the tissue at close proximity. Thus, during in vivo investigation the impedance measurements can largely be independent of lumen diameters, blood volumes, and flow rates when the contact is made between microelectrodes and the endoluminal surface. In implemented embodiments, specimens that harbored oxidative stress were found to generate distinctly higher EIS values compared to the healthy tissues over a range of frequency from 100 Hz to 500 kHz; other frequency ranges may of course be utilized.

EIS sensors according to the present disclosure can be incorporated onto a steerable catheter. In an example, a portion of the EIS sensor (e.g., one that includes concentric bipolar microelectrodes) is attached to an inflatable balloon of the catheter. A remaining portion of the EIS sensor (e.g., a pair of electrical contact surfaces) is attached to another location of the catheter (e.g., a tube of the catheter). The catheter is steered into a body of a subject (e.g., a patient) such that the inflatable balloon is in proximity of a tissue. The inflatable balloon is inflated to contact the biological tissue. Thus, the EIS sensor (e.g., the concentric bipolar microelectrodes) also becomes in contact with the tissue. EIS measurements is performed using the EIS sensor to detect a lesion of the tissue. Additional EIS measurements can also be performed at multiple sites for a single lesion to generate a contour map containing both topographical and electrochemical information. The EIS measurements can be potentially incorporated with intracardiac echocardiogram, optical coherence tomography (OCT), and/or micro-thermal sensors to further enhance the sensitivity and specificity for the assessment of pro-inflammatory states or unstable plaque.

FIG. 1 illustrates an example EIS-based diagnostic system 100 for diagnosing a lesion of a tissue. As illustrated, the EIS-based diagnostic system 100 includes an EIS sensor 110, a catheter 120, an electrical cable 130 (e.g., a coaxial cable), and an analysis system 140. The catheter 120 includes an inflatable balloon 122. In an example, the inflatable balloon 122 is located at an end (e.g., a tip) of the catheter 120. Concentric bipolar microelectrodes of the EIS sensor 110 are attached to the inflatable balloon 122. A pair of electrical contact surfaces of the EIS sensor 110 is attached to another location of the catheter 120 (e.g., to locations on the catheter's tube) and is connected to an end of the electrical cable 130. The other end of the electrical cable 130 is connected to the analysis system 140.

Generally, the catheter 120 is steered such that the balloon 122 is in proximity of a biological tissue. Excitation voltage at a range of frequencies is applied through the concentric microelectrodes of the EIS sensor 110. The resulting impedance of the biological tissue is measured. The analysis system 140 analyzes the impedance to diagnose whether a lesion (or some other disease) exists at the respective location of the biological tissue.

Embodiments of the EIS sensor 110 and the catheter 120 are further described in the next figures. Turning to the details of the analysis system 140, the analysis system includes various components for facilitating the EIS measurements and the diagnostic of the lesion. In an example, the electrical cable 130 provides an electrical connection to various components of the analysis system 140 such that voltage is supplied from the analysis system 140 and such that the resulting impedance is captured by the analysis system 140.

The analysis system 140 includes a voltage supply or a connector (e.g., a relay) to provide voltage from a remote voltage supply. The voltage supply (whether local or remote) can be a suitable waveform generator capable of supplying AC voltage of a desired frequency, e.g., between 100 Hz and 500 kHz inclusively.

The analysis system 140 also includes or interfaces with various components for measuring impedance across the concentric microelectrodes of the EIS sensor 110. For example, a potentiostat, or some other impedance measuring device, is used for taking EIS measurements of the impedance of the biological tissue and/or material in proximity to the concentric microelectrodes electrodes (e.g., non-obstructive and pro-inflammatory atherosclerotic lesions in human arteries). The impedance measurements can be used to detect the presence or absence of types of tissue or disease states, such as lesions, by correlating to or matching known measured impedances for such tissues and materials.

In addition, the analysis system 140 further includes a memory, a processor, and user input/output devices (e.g., a display, keyboard, mouse, etc.). Impedance data measured by the impedance device (e.g., the potentiostat) is provided to the memory. Any suitable memory can be used such as RAM and/or ROM memories. The memory hosts an analysis application that is executed by the processor. Any suitable processor can be used such as a general central processing unit (CPU). A user interface (UI) is available on one of the input/output devices (e.g., the display) to interface with the analysis application. Any suitable display, of any suitable size and/or type, can be used to provide the UI. The UI enables an operator of the EIS-based diagnostic system 100 to interface with the analysis application. This enables the presentation of impedance data, the diagnostic, and/or diagnostic-related data to the operator.

In an example, an impedance model is also stored as a part of the analysis application or hosted separately on the memory. The impedance model correlates impedances with lesions and/or other types of diagnostic for biological tissues. The analysis application compares the measured impedance data to the impedance model to output a diagnostic assessment (e.g., whether the lesion exists or not).

In another example, an impedance model need not be needed. Instead, the analysis application develops an impedance baseline by measuring impedances at different locations of the biological tissue or of a similar healthy biological tissue. Some or all of these locations may be known or suspected to be healthy (e.g., based on the locations or through an imaging diagnostic). Accordingly, the analysis application compares the measured impedance data to the impedance baseline to output the diagnostic assessment.

Figure 2:
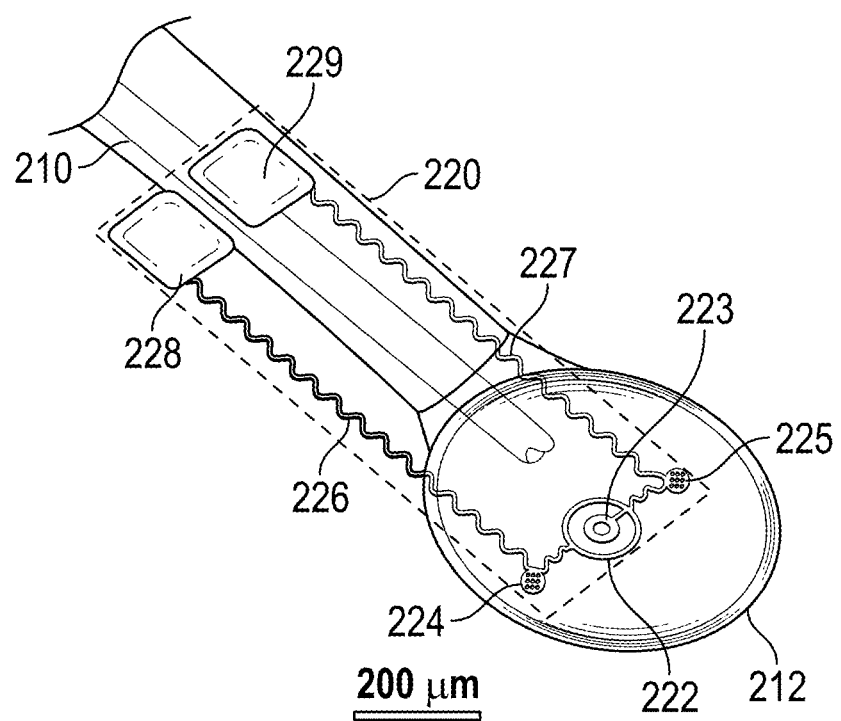
FIG. 2 illustrates an example portion of an electrical impedance apparatus, in accordance with an embodiment.

FIG. 2 illustrates an example embodiment of a portion of a catheter 210 and an EIS sensor 220 attached to such a catheter 210. The catheter 210 and the EIS sensor 220 are examples of the catheter 120 and the EIS sensor 110, respectively, of FIG. 1. The illustrated portion of the catheter 210 represents a tip and a section of the body of the catheter 210. An inflatable balloon 212 is part of the catheter 210 and is located at the tip. However, other locations of the catheter 210 can be used for the inflatable balloon 212.

Different attachment configurations are usable to attach the EIS sensor 220 to the catheter 210. In an example, the EIS sensor 220 is attached to the catheter 210 along two areas. The first area is a part of an outer surface of the balloon 212. The second area is not part of the balloon 212, but falls within the body of the catheter 210. As illustrated in FIG. 2, the dimensions of the balloon 212 and the EIS sensor 220 are in the micrometer range (e.g., between 100 µm and 1000 µm).

In particular, the EIS sensor 220 includes various components such as microelectrodes (shown as first microelectrode 222 and second microelectrode 223), attachment pads (shown as first attachment pad 224 and second attachment pad 225), electrical ribbon cables (shown as first electrical ribbon 226 and second electrical ribbon 227), and electrical contact surfaces (shown as first electrical contact surface 228 and second electrical contact surface 229). These components are further described in the next figures. As illustrated, the components are distributed along the balloon 212 and the portion of the catheter 220. The microelectrodes 222 and 223 and the attachment pads 224 and 225 are attached via, for example, biocompatible glue, to the balloon 212. On the other hand, the electrical contact surfaces 228 and 229 are attached via, for example, biocompatible epoxy (conductive or non-conductive) to the second area, such as to an area on the body of the catheter 210. At least respective portions of the electrical ribbon cables 226 and 227 are not attached to the catheter 210. Instead, these portions stand free and enable the electrical ribbon cables 226 and 227 to move with inflation and deflation of the balloon 212.

Figure 3:
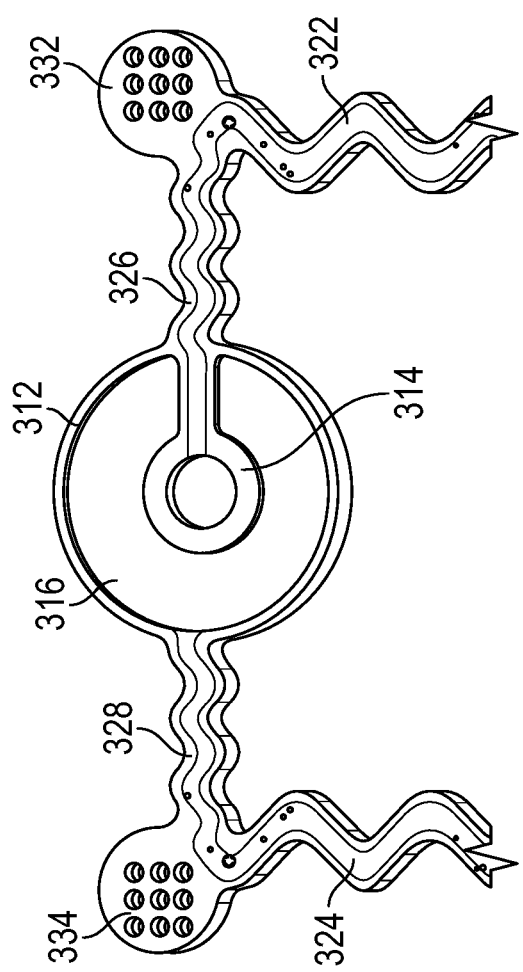
FIG. 3 illustrates an example portion of an electrical impedance sensor, in accordance with an embodiment.

FIG. 3 illustrates an example portion of an EIS sensor. The illustrated portion corresponds to, for instance, the portion of the EIS sensor 220 that is attached to the balloon 212 of FIG. 2. As illustrated, the portion of the EIS sensor includes a set of microelectrodes, a set of attachment pads, and a set of electrical ribbon cables. The respective dimensions are in the micrometer range.

The set of microelectrodes include two or more concentric microelectrodes. As illustrated an outer electrode 312 and an inner electrode 314 are disposed in a concentric configuration. The inner electrode 314 disposed in a flat, circular ring. The outer electrode 312 is also disposed in a flat, circular ring. The outer electrode 312 is concentric to the inner electrode 314 and substantially surrounds the inner electrode 314 (e.g., fully with the exception of the locations for interfacing with the electrical ribbon cables. For example, this includes the outer electrode 312 surrounding the inner electrode 314 more than 66%, 75%, 80%, 90%, 95%, or otherwise as known in the art). Each of the two electrodes is made of a highly conductive electric material and has a substantially circular shape. In use, the two microelectrodes have opposite polarities, thereby providing a configuration of concentric bipolar microelectrodes. In an example, the set of microelectrodes are disposed on and/or are within a non-conductive section 316 of the EIS sensor, such as one made of parylene. The non-conductive section 316 has a circular shape, or some other shape, and is large enough to contain the set of microelectrodes. The non-conductive section 316 can be, optionally, attached to the underlying balloon via, for instance, a biocompatible glue.

The set electrical ribbon cables is connected to the set of microelectrodes such that electrical power is supplied to the microelectrodes via the electrical ribbon cables. In an example, the set electrical ribbon cables includes a pair of electrical ribbon cables (shown as a first ribbon cable 322 and a second ribbon cable 324). An end of one the ribbon cables (e.g., the first ribbon cable 322) is connected to the inner electrode 314. An end of the other ribbon cable (e.g., the second ribbon cable 324) is connected to the outer electrode 312. In addition, the set of electrical ribbon cables has a configuration that supports the inflation and deflation of an underlying balloon of a catheter. One example configuration shown in FIG. 3 includes electrical ribbon cables that have respective serpentine lengths. This example configuration enables movement of the cables in different directions (e.g., X and Y directions of a plane). Other example configurations are also possible and include, for instance, electrical ribbon cables that have slack (e.g., additional length that is sufficient to allow the inflation and deflation of the balloon).

The set of attachment pads is an example of an interface for attaching the illustrated portion of the EIS sensor to the underlying balloon. The attachment can be adhesive. For example, the attachment uses a biocompatible glue that is applied between the outer surface of the underlying balloon and lower surface (or the interfacing side) of the attachment pads. In an example, the set of attachment pads include a pair of attachment pads (shown as a first attachment pad 332 and a second attachment pad 334). Each of the attachment pads represents a meshed pad with a certain hole pattern. FIG. 3 illustrates a 3×3 hole pattern, although other patterns can be similarly used. The hole pattern improves the adhesiveness of the attachment. Generally, the attachment pads are made of a non-conductive material.

In an example, each of the attachment pads is connected to (e.g., on one side) or is a protruding part of one of the electrical ribbon cables. In other words, one of the electrical ribbon cables (e.g., the first electrical ribbon cable 322) extends radially from the inner electrode 314 to one of the attachment pads (e.g., the first attachment pad 332). As such, a portion 326 of that electrical ribbon cable 322 can run between the inner electrode 314 and the attachment pad 332. That portion 326 can be optionally attached to the underlying balloon via, for example, a biocompatible glue. However, a remaining portion of the electrical ribbon cable is generally not attached to the underlying balloon. Similarly, the other electrical ribbon cable 324 extends radially from the outer electrode 312 to another one of the attachment pads (e.g., the second attachment pad 334) and a portion 328 thereof can be, optionally, attached to the underlying balloon.

Figure 4:
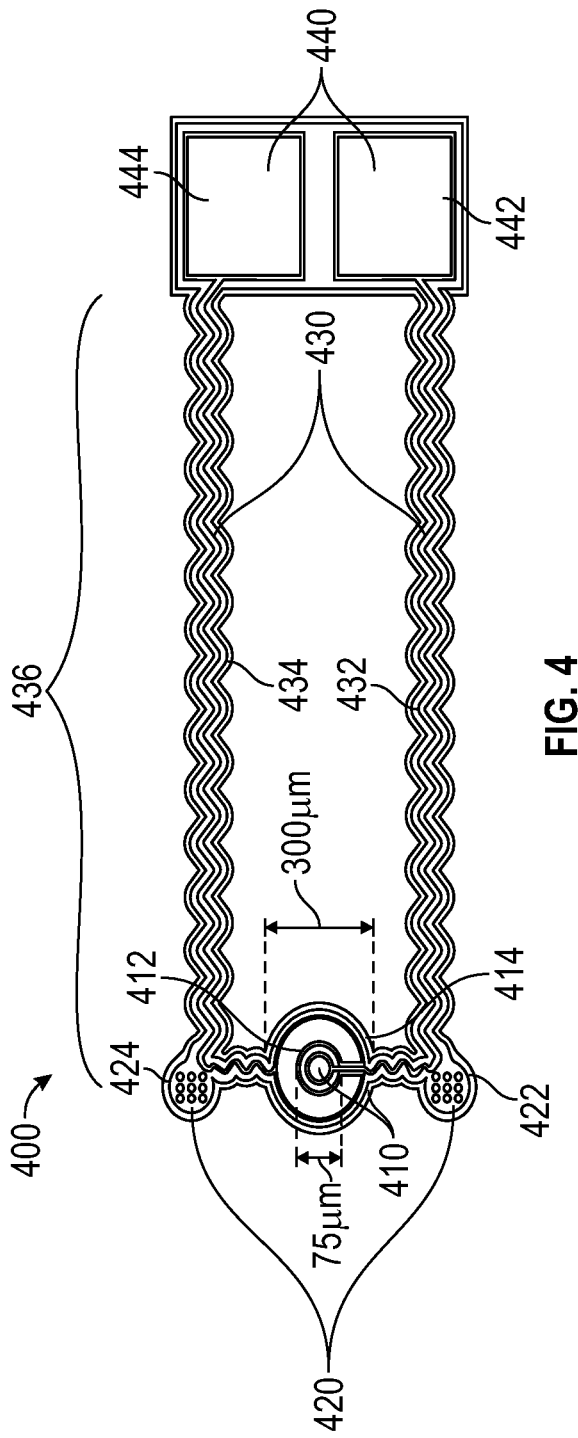
FIG. 4 illustrates an example electrical impedance sensor, in accordance with an embodiment.

FIG. 4 illustrates a top view of an EIS sensor 400. The EIS sensor 400 is an example of the EIS sensor 220 of FIG. 2. As illustrated, the EIS sensor 400 includes concentric bipolar microelectrodes 410, a pair of attachment pads 420, a pair of electrical ribbon cables 430, and a pair of electrical contact surfaces 440. The concentric bipolar microelectrodes 410 include an inner electrode 412 and outer electrode 414. In an example, the inner dimension of the inner electrode 412 is about 75 µm. In comparison, the outer diameter of the outer electrode 414 is about 300 µm. The pair of electrical ribbon cables 430 connects the concentric bipolar microelectrodes 410 to the electrical pair contact surfaces 440. For example, one of the electrical cable ribbons (shown as electrical ribbon cable 432) connects the inner electrode 412 to one of the electrical contact surfaces (shown as electrical contact surface 442). Similarly, the other electrical cable ribbon (shown as electrical ribbon cable 434) connects the outer electrode 414 to the other electrical contact surface (shown as electrical contact surface 444). In addition, the attachment pads are disposed at respective locations of the electrical ribbon cables. For example, one of the attachment pads (shown as attachment pad 422) is attached to or protrudes from the electrical ribbon cable 432. Similarly, the other attachment pad (shown as attachment pad 424) is attached to or protrudes from the electrical ribbon cable 434.

Conductive and non-conductive materials are used to fabricate these components of the EIS sensor 400, as further described in FIG. 13. Generally, the conductive materials are highly electrical conductive metals, such as gold and/or platinum. The non-conductive materials are biocompatible polymers with high electrical insulation, such as parylene. As illustrated, the electrically conductive portions of the electrical contact surfaces, electrical ribbon cables, and concentric bipolar microelectrodes 410 are made of the same highly conductive metal. The electrically non-conductive portions of the electrical contact surfaces, electrical ribbon cables, attachment pads, concentric bipolar microelectrodes 410 and remaining electrically non-conductive portions of the sensor 410 are made of the same biocompatible polymer with high electrical insulation.

FIG. 4 also illustrates that each electrical ribbon cable has a serpentine length 436. In an example, the serpentine length is implemented as a sinusoidal configuration. For each of the electrical ribbon cables, the sinusoidal configuration can be applied throughout the entire electrical ribbon cable (e.g., between a respective microelectrode and an electrical contact surface) or throughout a section thereof (e.g., between a respective attachment pad and an electrical contact surface). The sinusoidal configuration allows movement of the electrical ribbon cable in, for example, X and Y directions of a plane. Other configurations to support such movement are also possible, such as a coiled configuration or one that includes additional wire slack. In addition, each of the electrical ribbon cables can have multiple serpentine lengths. At least one of the multiple serpentine lengths of a cable has a different wavelength than another wavelength of the multiple serpentine lengths of the cable. For example, and as shown in FIG. 4, the electrical ribbon cable 434 has two different wavelengths. One wavelength occurs for the portion of the electrical ribbon cable 434 between the outer electrode 414 and the attachment pad 424. The other wavelength occurs for the portion of the remaining portion of the electrical ribbon cable between the attachment pad 424 and the electrical contact surface 444. Further the two electrical ribbon cables can have different lengths because of the respective connections to the microelectrodes. As shown in FIG. 4, the electrical ribbon cable 432 connected to the inner electrode 412 is longer than the other electrical ribbon cable 434 connected to the outer electrode 414 because the inner electrode 412 is smaller than the outer electrode 414.

Figure 5:
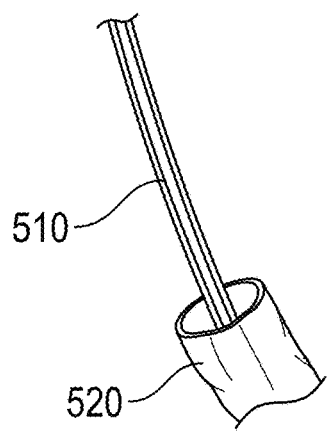
FIG. 5 illustrates an example insertion of an electrical impedance apparatus into an aorta, in accordance with an embodiment.

FIG. 5 illustrates an example insertion of a portion 510 of a catheter into an aorta 520 of a subject (e.g., ex vivo rabbit aorta). The inserted portion 510 corresponds to the illustrated portion of the catheter 210 of FIG. 2. In particular the inserted portion 510 includes a portion of the catheter's body, the catheter's inflatable balloon, and an EIS sensor attached to the catheter (e.g., more specifically to the inflatable balloon and a location of the catheter's body). In an example, the inflatable balloon is deflated, the portion 510 of the catheter is inserted into the aorta 520, and the inflatable balloon is inflated subsequently.

Figure 6:
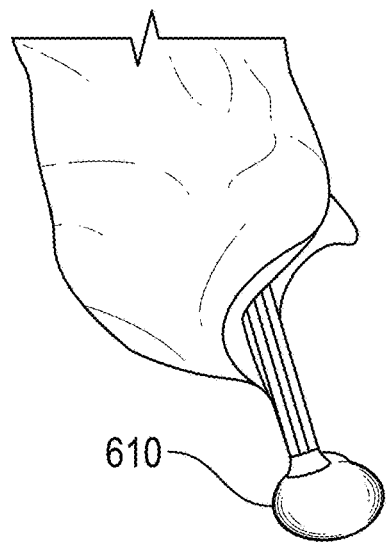
FIG. 6 illustrates an example inflation of a balloon of a catheter with respect to an aorta, in accordance with an embodiment.

FIG. 6 illustrates an example of the inflatable balloon of FIG. 5 upon inflation (shown as "inflatable balloon 610"). Of course, as explained in connection with FIG. 5, the inflatable balloon 610 is typically inflated after insertion into the aorta. However, FIG. 6 shows the inflatable balloon 610 in the inflated state for illustrative purposes. Generally, the inflatable balloon 610 is inflated to create a balloon volume large enough for contact between the outer surface of the inflatable balloon 610 and an inner surface of the aorta (or an intima of the aorta). A pressure between five and nine pounds per square inch (psi) (e.g., about 34,000 to 62,000 Pa) provides a sufficient inflation range with respect to aortas. Other pressure ranges can be similarly used for other types of tissues and can depend on the volume of the inflatable balloon 610.

Figure 7:
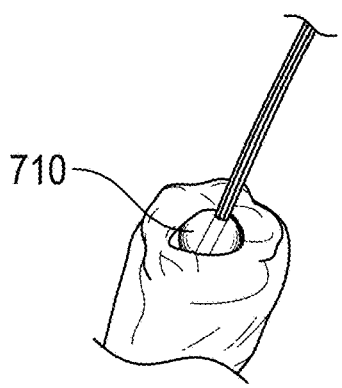
FIG. 7 illustrates an example insertion of an electrical impedance apparatus into an aorta and inflation of a balloon inside the aorta, in accordance with an embodiment.

FIG. 7 illustrates an example of the inflatable balloon of FIG. 5 inserted into the aorta and subsequently inflated (shown as "inflatable balloon 710"). As illustrated, the outer surface of the inflatable balloon 710 contacts the inner surface of the aorta upon inflation of the inflatable balloon 710. The concentric bipolar microelectrodes of the EIS sensor are also disposed at the outer surface of the inflatable balloon 710. As such, the concentric bipolar microelectrodes also contact the inner surface of the aorta, thereby allowing more accurate EIS measurements of the aorta's impedance.

Figure 8A:
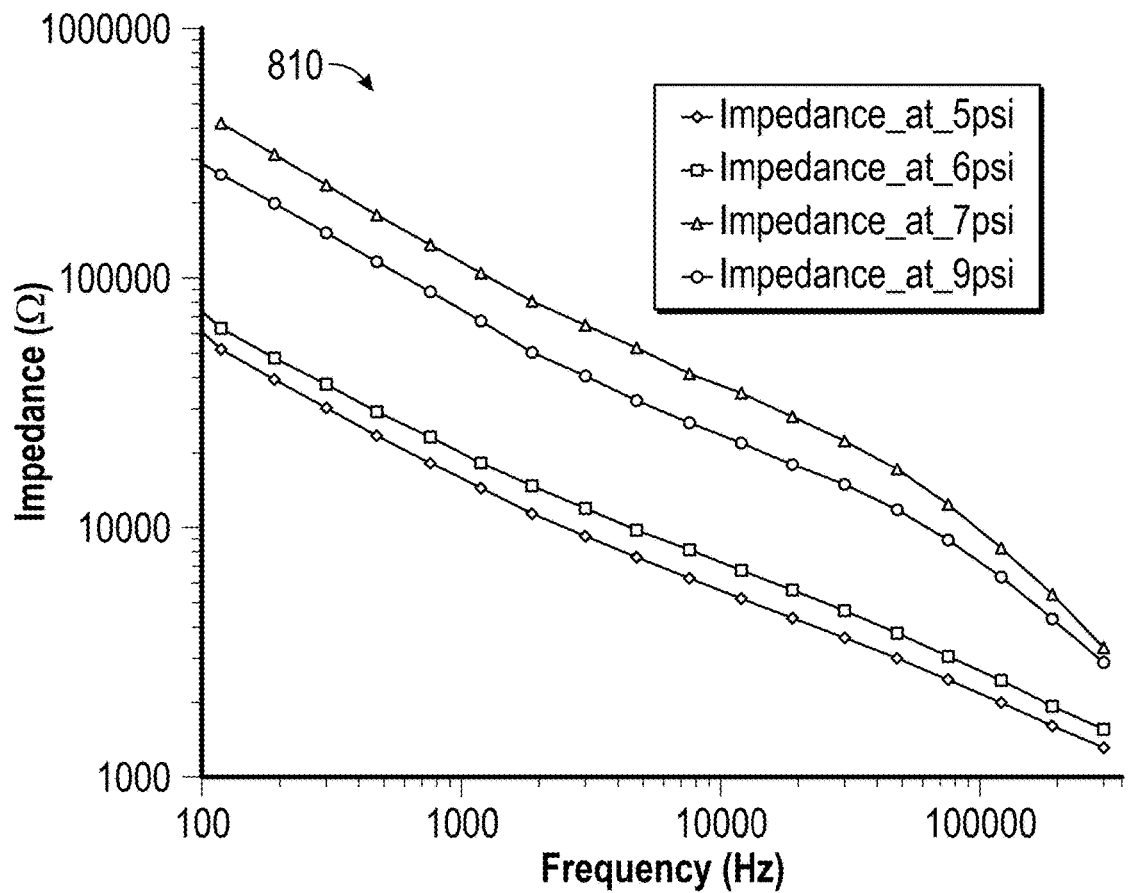
FIGS. 8A and 8B illustrate example measured impedances at different inflations of a balloon, in accordance with an embodiment.
Figure 8B:
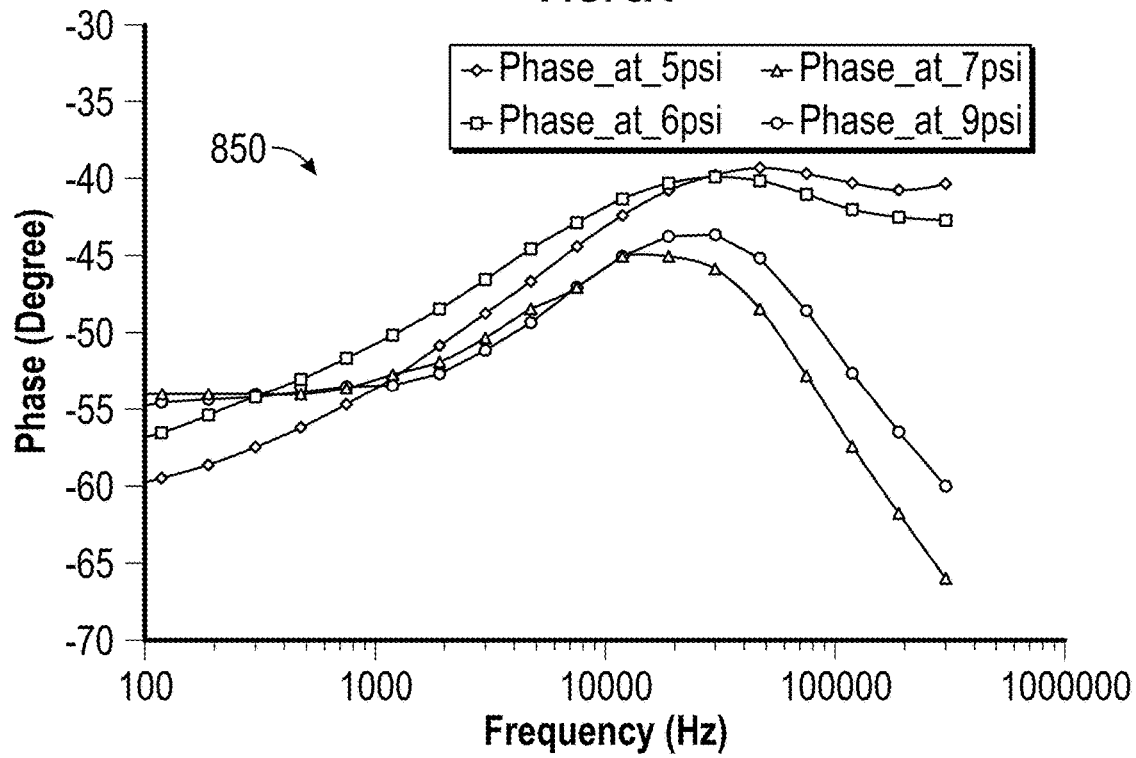

FIGS. 8A and 8B illustrate characterizations of impedance at different inflation levels of an inflatable balloon, such as the inflatable balloon 710 of FIG. 7. Generally, the impedance is characterized using the magnitude 810 (shown in FIG. 8A) and phase 850 (shown in FIG. 8B) of the impedance over a frequency range. The impedance changes with the inflation level of the inflatable balloon because of the resulting contact between the outer surface of the inflatable balloon and the inner surface of the tissue (e.g. the aorta's wall).

As illustrated, impedance data is collected in response to balloon inflation at five, six, seven, and nine psi, respectively (e.g., about 34,000, 41,000, 48,000, and 62,000 Pa, respectively). The impedance data reveals that about seven psi (e.g., about 48,000 Pa) is sufficient for adequate contact between the EIS sensor (e.g., the concentric bipolar microelectrodes) and the inner surface of the tissue. In particular, at seven psi (e.g., about 48,000 Pa) and relative to other inflation levels, the impedance data shows a significant change in the magnitude over the whole frequency range and a significant change in the phase at frequencies above 30 kHz. At nine psi (e.g., about 62,000), the balloon may be over-inflated representing a relatively slight decrease.

Impedance measurements, similar to the ones of FIGS. 8A and 8B, can be repeated for different tissue types, tissue dimensions, inflatable balloon dimensions, and/or EIS sensor dimensions and/or configurations. The measurements allow the development of guidelines for using certain EIS sensor-inflatable balloon combinations and for inflating the inflatable balloon to an appropriate level given a tissue type or a tissue dimension. These guidelines can be added to an impedance model for use by an analysis tool, such as the analysis tool of the EIS-based diagnostic system 100 of FIG. 1.

Figure 9A:
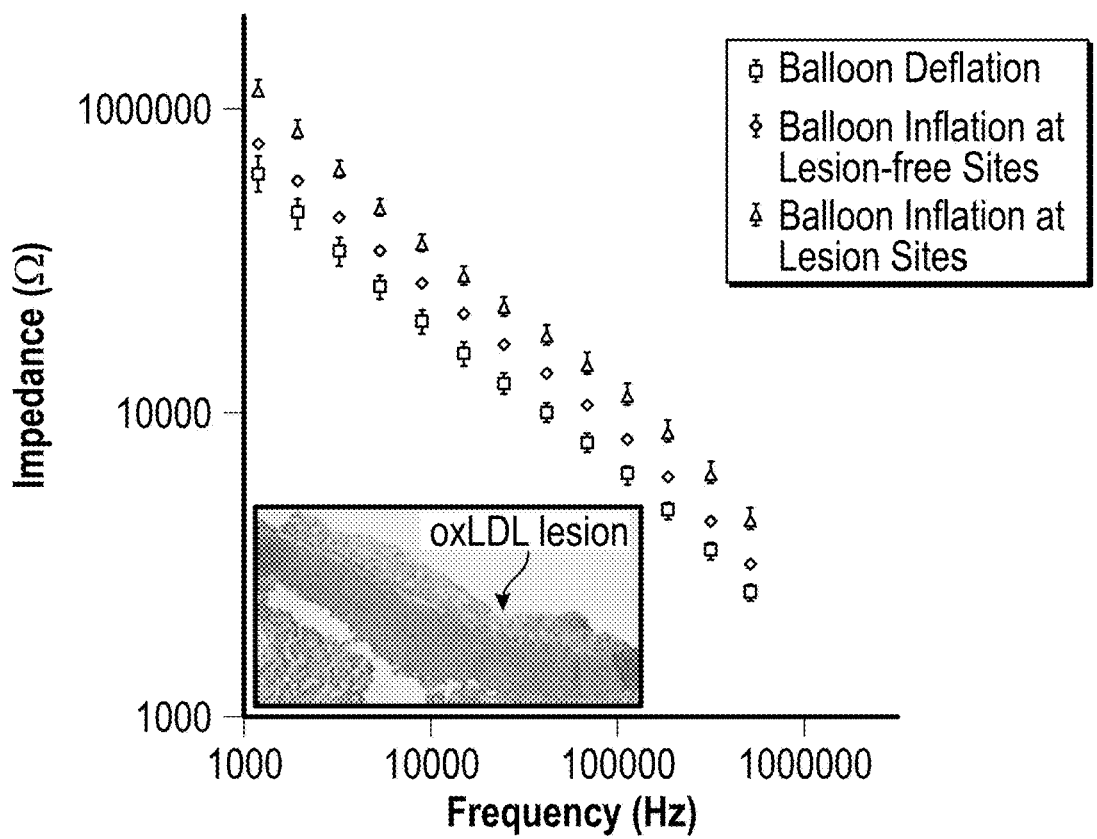
FIGS. 9A and 9B illustrate example measured impedances of a tissue based on an inflation and deflation of a balloon, in accordance with an embodiment.
Figure 9B:
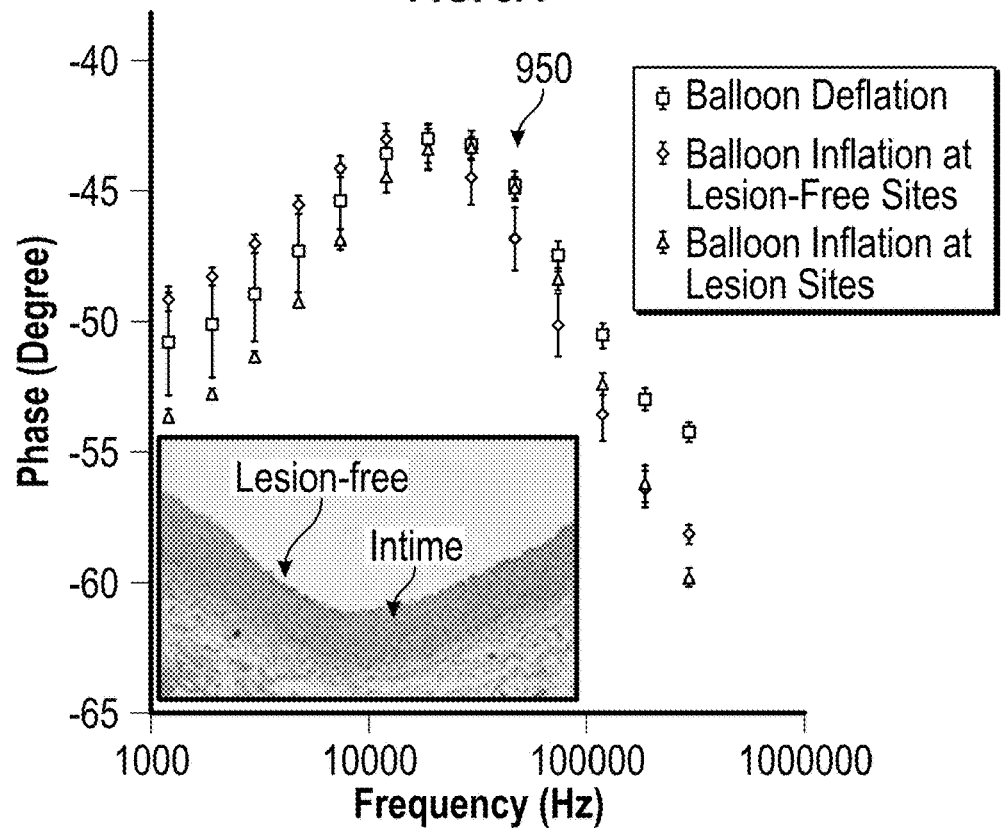

FIGS. 9A and 9B illustrate a diagnostic of a lesion of a tissue. The lesion is diagnosed by taking impedance measurements using a catheter that includes an inflatable balloon and an EIS sensor, as described herein. In particular, the impedance is characterized in magnitude 910 (as shown in FIG. 9A) and phase 950 (as shown in FIG. 9B) over a frequency range. The impedance is compared to an impedance of a healthy tissue (e.g., a tissue known to be lesion-free). Differences between the two impedance falling over a threshold identify the presence of the lesion.

The impedance of the lesion-suspect tissue is measured by inserting the catheter, inflating the balloon to an appropriate level, and performing EIS measurements. In comparison, various techniques are usable for developing the impedance of the healthy tissue. One example technique involves performing similar EIS measurements to develop a baseline. The baseline can be developed for a current use (e.g., for comparison to the impedance of the lesion-suspect tissue) and/or for a future use. In the future use case, the baseline is stored in an impedance model. As such, for any future diagnostic of a lesion-suspect tissue, it may be sufficient to perform EIS measurements for that tissue and to compare the measurements to the already developed impedance of the impedance model. In another example technique, a similar baseline is developed when the inflatable balloon is deflated. The tissue can be lesion-free or can have a lesion. Either baselines (e.g., the one developed with a lesion-free tissue and an inflated balloon or the one developed with a deflated balloon) are usable to diagnose the lesion. The usage difference between the two baselines is that the threshold for the deviation will change. In general, the threshold is relatively larger for the baseline that uses a deflated balloon.

As illustrated in FIGS. 9A and 9B, aortas of ex vivo rabbits are used. After eight weeks of high-fat diet, oxLDL lesions are developed. The rabbits are sacrificed, and aortas are extracted and fixed in fifteen percent paraformal aldehyde (PFA). The individual aortas are sectioned into two to three centimeter segments and immersed in phosphate buffer saline (PBS) for deployment of the catheter having the inflatable balloon and the EIS sensor.

After the balloon inflation, impedance measurements are taken. Deviations between the impedances of an aorta that has an oxLDL lesion and an aorta that is lesion free are detected. The deviations allow the diagnosis of the oxLDL lesion. For example and as shown in FIG. 9A, an increase in the magnitude 910 of the impedance over the entire frequency range from 1 kHz to 1,000 kHz identifies the oxLDL lesion (e.g., the tissue that results in the higher impedance magnitude is the tissue that has the oxLDL lesion). The results of this EIS-diagnostic of the oxLDL lesion are confirmed by performing a histology of the aorta walls. The histology shows Endoluminal lipid deposition or atherosclerotic lesions of the aorta that has the higher impedance magnitude. The histology also shows that the other aorta that has the lower impedance magnitude is lesion free.

As such, tissue diseases (e.g., lesions and other diseases) can be accurately diagnosed by using a catheter that has an inflatable balloon and an EIS sensor as shown in FIGS. 8A, 8B, 9A, and 9B. In an example, an analysis tool uses an impedance model. For a type and/or dimension of a tissue, the impedance model specifies the EIS sensor-inflatable balloon combination to use and the inflation level of the inflatable balloon, as shown in FIGS. 8A and 8B. In addition, the impedance model includes and establishes an impedance baseline of a disease-free tissue and/or of a deflated balloon. The comparison of measured impedances via the impedance baseline(s) diagnoses whether a disease is present or not, as shown in FIGS. 9A and 9B.

Figure 10:
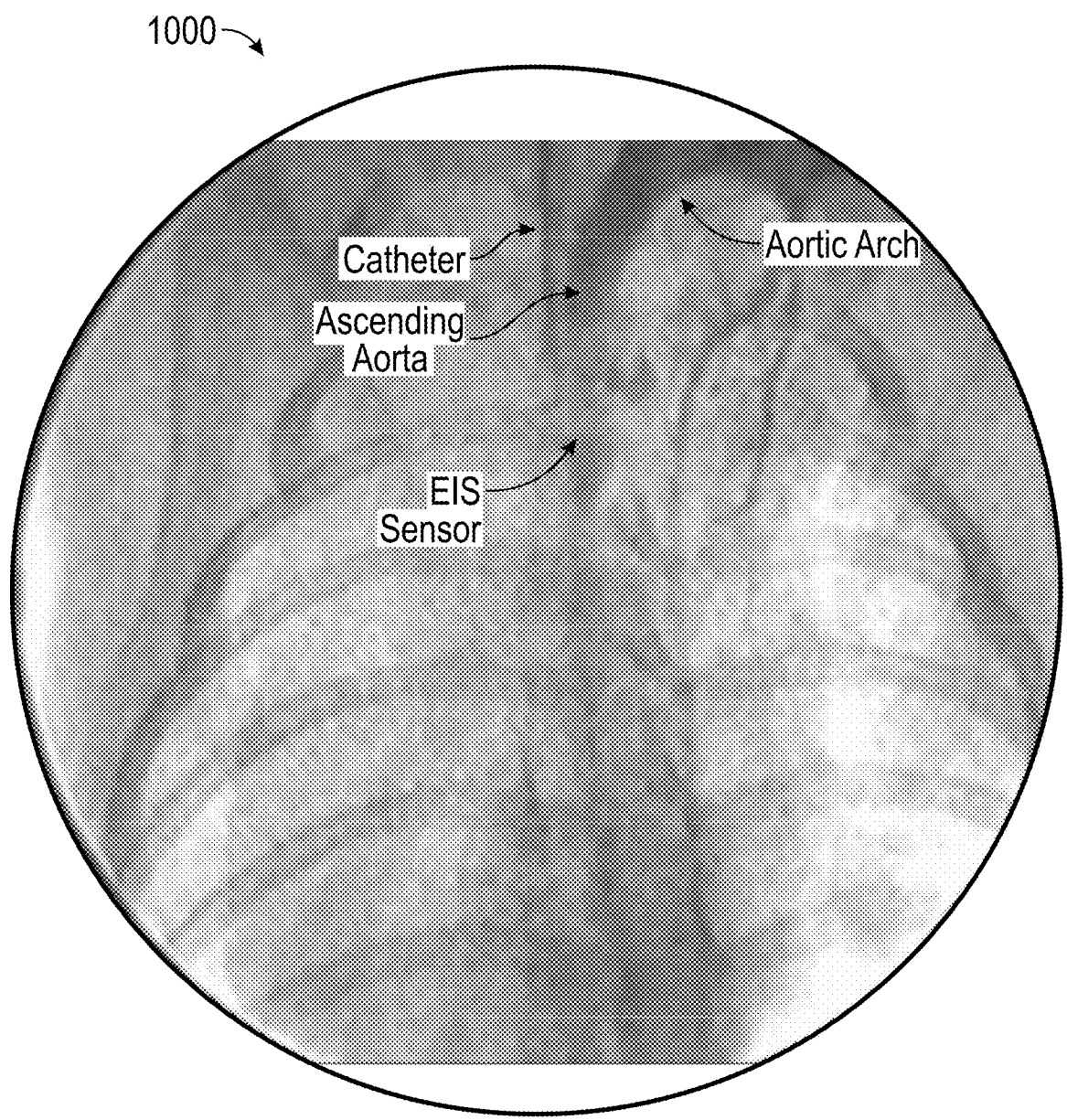
FIG. 10 illustrates an example of guiding a catheter such that a balloon is in proximity of a tissue, in accordance with an embodiment.

FIG. 10 illustrates an example use 1000 of the EIS diagnostic-based technique in an in vivo subject such as a rabbit. As illustrated, the example use 1000 deploys a catheter that includes an inflatable balloon and an EIS sensor into the body of the subject. Fluoroscopy is used to guide the deployment such that the inflatable balloon and EIS sensor become in proximity of a carotid artery. The catheter is deployed through a right carotid artery cut-down. The inflatable balloon is then inflated such that the EIS sensor contacts the surface of the carotid artery. The impedance of carotid artery's surface is measured via the EIS sensor.

Figure 11A:
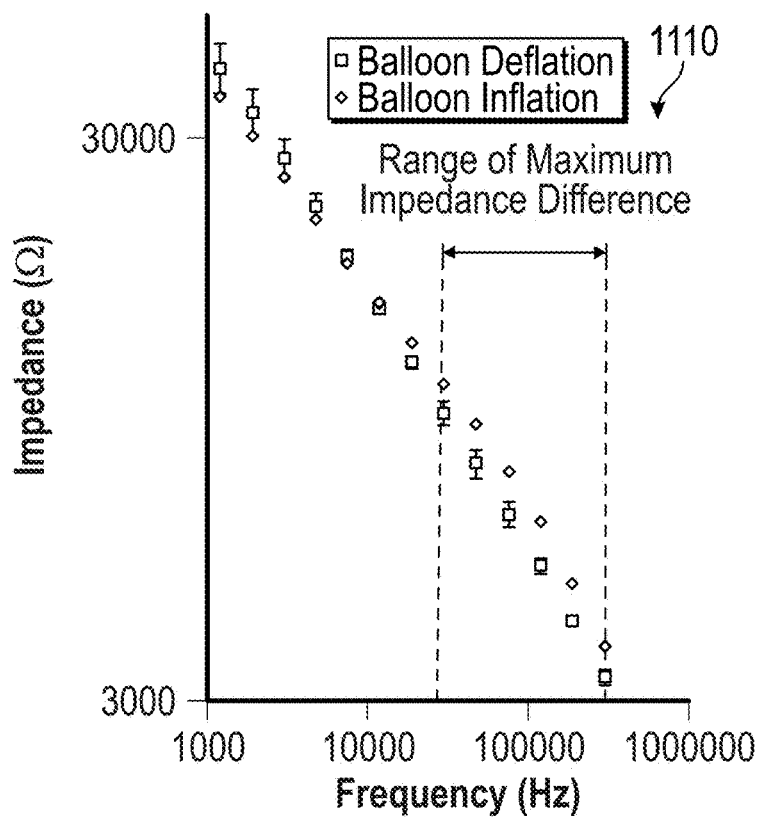
FIGS. 11A and 11B illustrate example measured impedances of a lesion at different inflations of a balloon, in accordance with an embodiment.
Figure 11B:
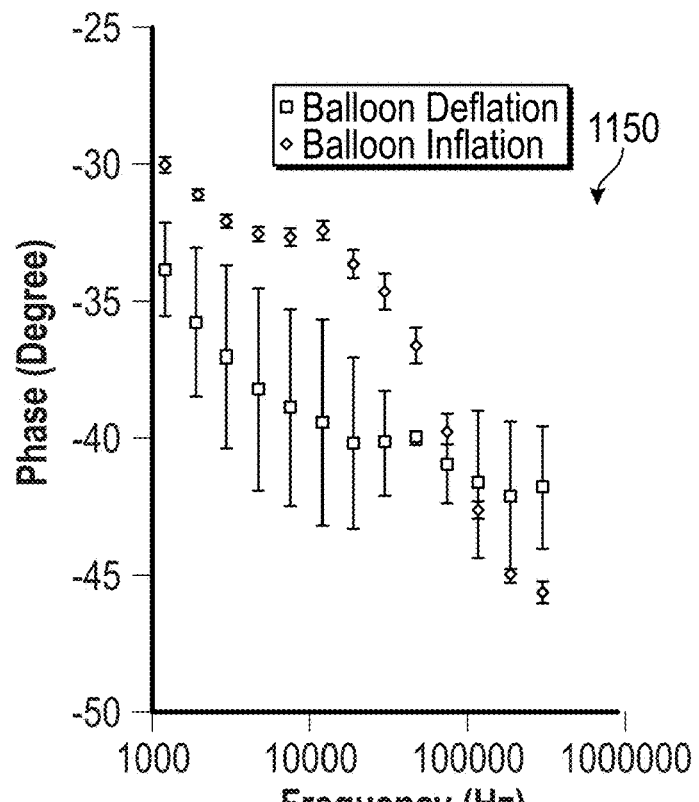
Figure 12A:
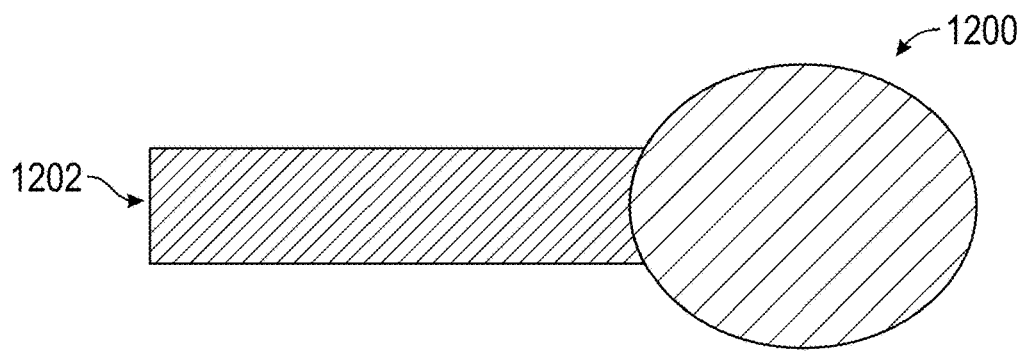
FIGS. 12A, 12B, 12C, and 12D illustrate an example fabrication of a balloon, in accordance with an embodiment.
Figure 12B:
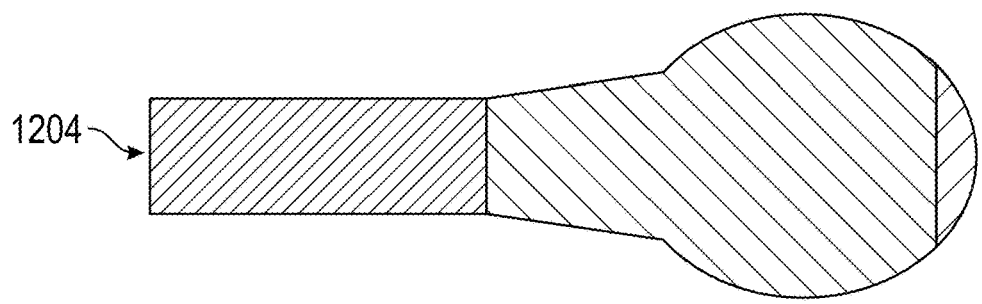
Figure 12C:
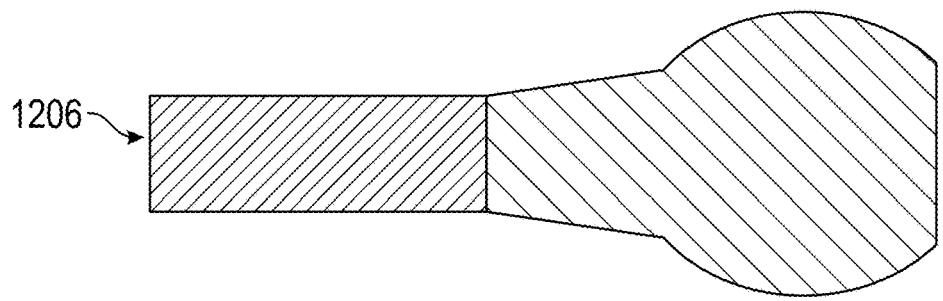
Figure 12D:
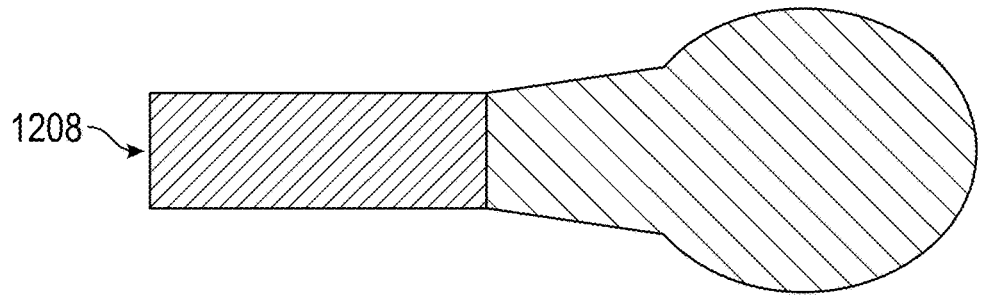
Figure 13A:
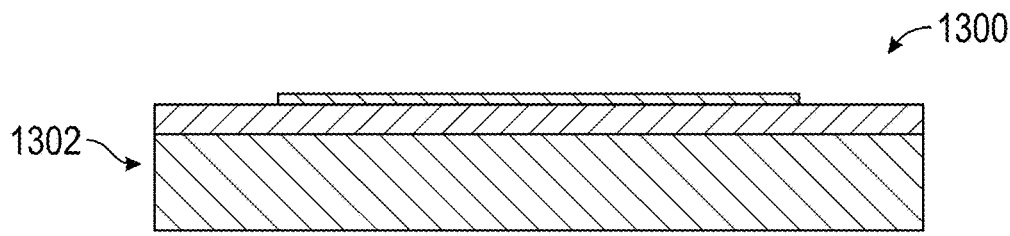
FIGS. 13A, 13B, 13C, and 13D illustrate an example fabrication of an electrical impedance sensor, in accordance with an embodiment.
Figure 13B:
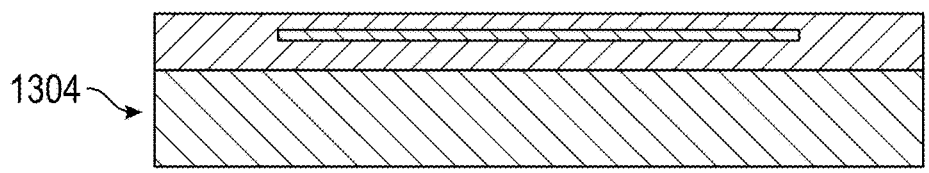
Figure 13C:
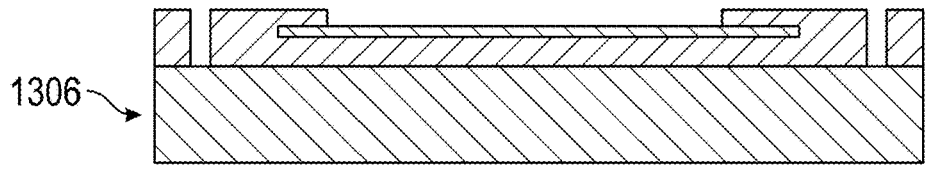
Figure 13D:

FIGS. 11A and 11B illustrate the measured impedance of the carotid artery's surface described in connection with FIG. 10. When compared to the impedance measurements of the deflated balloon (e.g., a baseline), the impedance measured with the inflated balloon shows significant increase in the magnitude 1110 (as shown in FIG. 11A) of the impedance at a frequency from 10 kHz to 300 kHz, along with the distinct characteristics of the phase 1150 (as shown in FIG. 11B). These deviations from the baseline indicate the presence of a lesion.

Turning to FIGS. 12A through 14B, the figures illustrate example fabrications of an inflatable balloon of a catheter and EIS sensor and example assembly of the two. When assembled, the inflatable balloon, the EIS sensor, and the catheter form an apparatus for EIS measurements. The apparatus base can be used as a part of the EIS-based diagnostic system 100 of FIG. 1.

FIGS. 12A, 12B, 12C, and 12D illustrate an example fabrication 1200 of the inflatable balloon. The fabrication 1200 includes multiple fabrication steps. In a first fabrication step 1202 (shown in FIG. 12A), a droplet of photoresist (PR) is formed at a location of the catheter. In an example, the location corresponds to an end (e.g., the tip) of the catheter. In a second fabrication step 1204 (shown in FIG. 12B), a biocompatible polymer coats partially (e.g., 75% to 95%) the PR droplet. The polymer can be expanded under pressure such that the fabricated balloon is an inflatable balloon. An example of the polymer is silicone. The coating is partial to allow a tip of the PR droplet to be opened. In a third fabrication step 1206 (shown in FIG. 12C), the PR is removed. The PR removal results in a partial droplet (e.g., a droplet with an open tip) that is made of the polymer material (e.g., silicone). In a fourth fabrication step 1208 (shown in FIG. 12D), the partial droplet is turned into a full droplet using the polymer. For example, the open tip is sealed with silicone. The full droplet corresponds to a fabricated inflatable balloon.

FIGS. 13A, 13B, 13C, and 13D illustrate an example fabrication 1300 of the EIS sensor. The fabrication 1300 includes multiple fabrication steps. In a first fabrication step 1302 (shown in FIG. 13A), a first layer of electrically non-conductive material is deposited on a substrate. In an example, the material includes parylene such as parylene C. The substrate includes a hexamethyldisilane (HDMS) substrate. In also the first fabrication step 1302, an electrically conductive material is deposited on a portion of the first layer of the non-conductive material. For example, highly conductive metal such as gold or platinum, or some other metal alloy, is deposited over a portion of the parylene material. The metal is patterned to form the desired configuration of the electrically conductive portions of concentric bipolar electrodes, electrical ribbon cables, and electrical contact surfaces. In a second fabrication step 1304 (shown in FIG. 13B), a second layer of the non-conductive material is deposited on the conductive material. For example, a second layer of the parylene material is deposited over the conductive metal layer. This second layer coats and seals the conductive layer. In a third fabrication step 1306 (shown in FIG. 13C), lithography is applied to a first portion and a second portion of the second layer of the non-conductive material. The first portion corresponds to terminal ends of the EIS sensor. The second portion corresponds to the attachment pads of the EIS sensor. In also the third fabrication step 1306, other portions of the second layer of the non-conductive material are etched. These other portions correspond to the outer electrode, the inner electrode, the attachment pads, edges of the electrodes and the electrical ribbon cables, and conductive portion of the electrical contact surfaces of the EIS sensor. For example, $O_2$ plasma etching is applied to the second parylene layer to open the sensor electrodes and the contact surfaces, and to define the edges of the EIS sensor and the electrical ribbon cables. In a fourth fabrication step 1308 (shown in FIG. 13D), the EIS sensor is removed from the substrate. For example, the EIS sensor is lifted off from the HDMS substrate. The resulting terminal ends of the EIS sensor are free-standing.

Figure 14A:
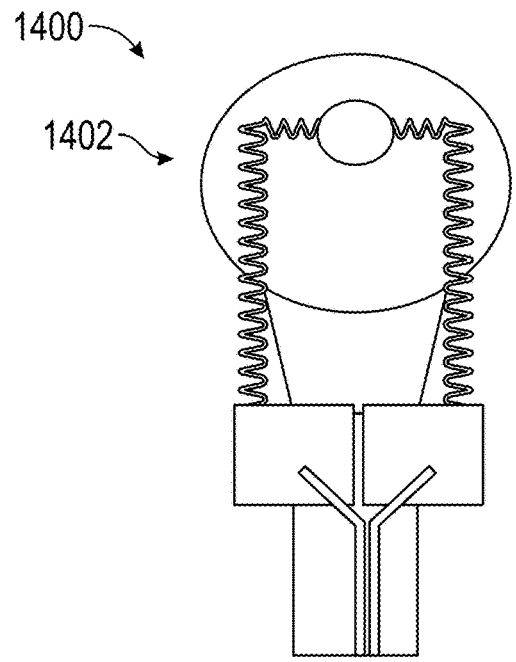
FIGS. 14A and 14B illustrate an example assembly of a balloon and an electrical impedance sensor, in accordance with an embodiment.
Figure 14B:
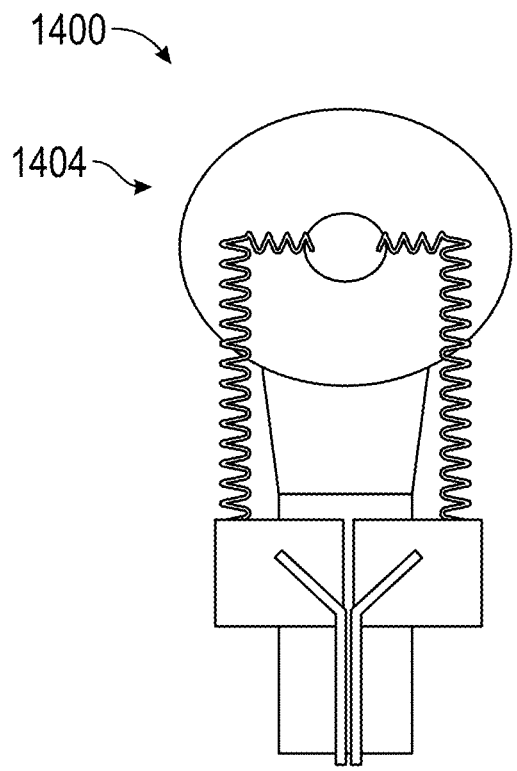

FIGS. 14A and 14B illustrate an example assembly 1400 of fabricated inflatable balloon and EIS sensor. The assembly 1400 includes multiple assembly steps. In a first assembly step 1402 (shown in FIG. 14A), the EIS sensor is attached to the inflatable balloon. In an example, the attachment occurs with the inflatable balloon being in a deflated state. The attachment includes, for instance, an adhesive attachments of the attachment pads of the EIS sensor to the outer surface of the inflatable balloon. The concentric bipolar microelectrodes and a portion of the electrical ribbon cables may also, but need not, be attached to the outer surface of the inflatable balloon. The adhesive attachment uses an electrically non-conductive biocompatible glue. In also the first assembly step 1402, the EIS sensor is attached to a remaining portion of the catheter, such as to a body of the catheter. For example, the electrical contact surface is adhesively attached to the body of the catheter. The adhesion may use the same or a different biocompatible glue. For example, the adhesion uses an electrically conductive or non-conductive epoxy. Wires of a coaxial cable can also be connected (e.g., electrically bonded or coupled) to the electrical contact surfaces in the first assembly step 1402. For example, a center signal wire of the coaxial cable is connected to one of the electrical contact surfaces. Similarly, a mesh ground wire of the coaxial cable is connected to the other electrical contact surfaces. In a second assembly step 1404 (shown in FIG. 14B), the inflatable balloon can be inflated to check for the quality of the assembly (e.g., whether the EIS sensor was properly attached to the catheter). For example, upon inflation, the attachments of the attachment pads to the inflatable balloon and of the contact surfaces to the body of the catheter are checked. In addition, the electrical ribbon cables are checked to see if such cables properly stretch in the X and Y directions of a plane.

Figure 15:
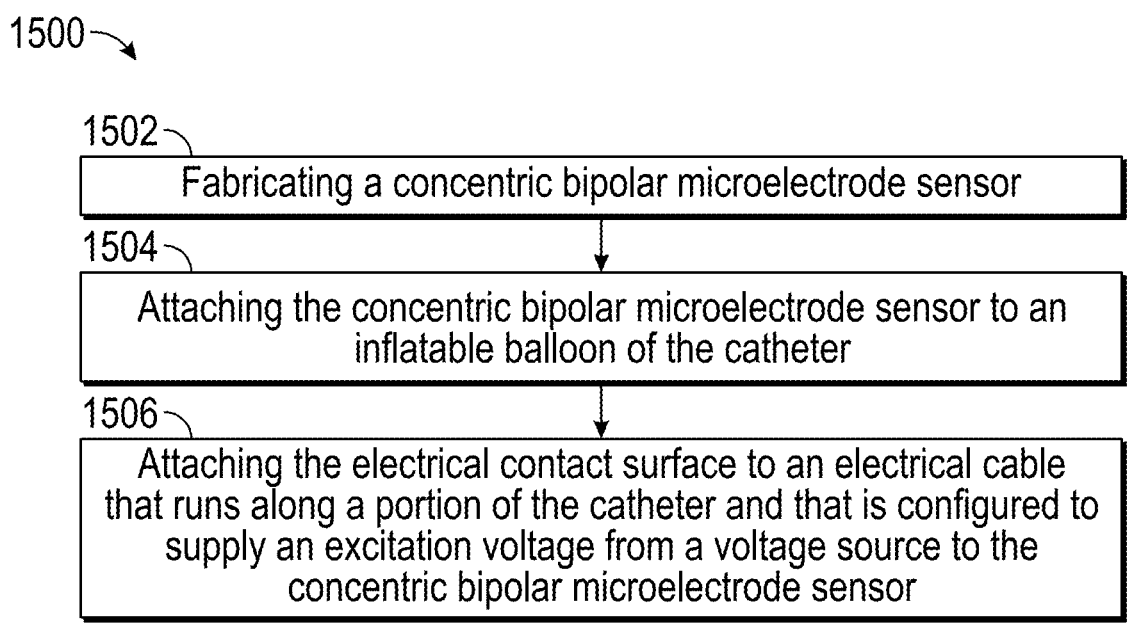
FIG. 15 illustrates an example manufacturing method of an electrical impedance sensor, in accordance with an embodiment.

FIG. 15 illustrates an example method of manufacturing of an apparatus for EIS measurement. The apparatus includes an EIS sensor and a catheter having an inflatable balloon, where the EIS sensor is attached to the catheter. The example method of manufacturing includes multiple operations.

In an operation 1502, an EIS sensor is fabricated. For instance, some or all of the fabrication steps of the example fabrication 1300 of FIG. 13 are performed to fabricate the EIS sensor.

In an operation 1504, the EIS sensor is attached to the catheter. The attachment includes attaching concentric bipolar electrodes of the EIS sensor to the inflatable balloon via, for example, attachment pads of the EIS sensor. The attachment also includes attaching electrical contact surfaces of the EIS sensor to another portion of the catheter. The attachment may be performed by following the example assembly 1400 of FIG. 14. The inflatable balloon may, but need not be, fabricated using the example fabrication 1200 of FIG. 12. For example, the catheter is acquired from another source and the inflatable balloon is fabricated. In another example, the catheter is acquired from the other source with the inflatable balloon already fabricated.

In an operation 1506, the electrical contact surfaces of the EIS sensor are connected to an electrical cable. The electrical cable runs along a portion of the catheter and is configured to supply an excitation voltage from a voltage source to the concentric bipolar microelectrodes of the EIS sensor. For example, the electrical cable includes a coaxial cable. Connecting the electrical cable may be performed by following the example assembly 1400 of FIG. 14.

Figure 16:
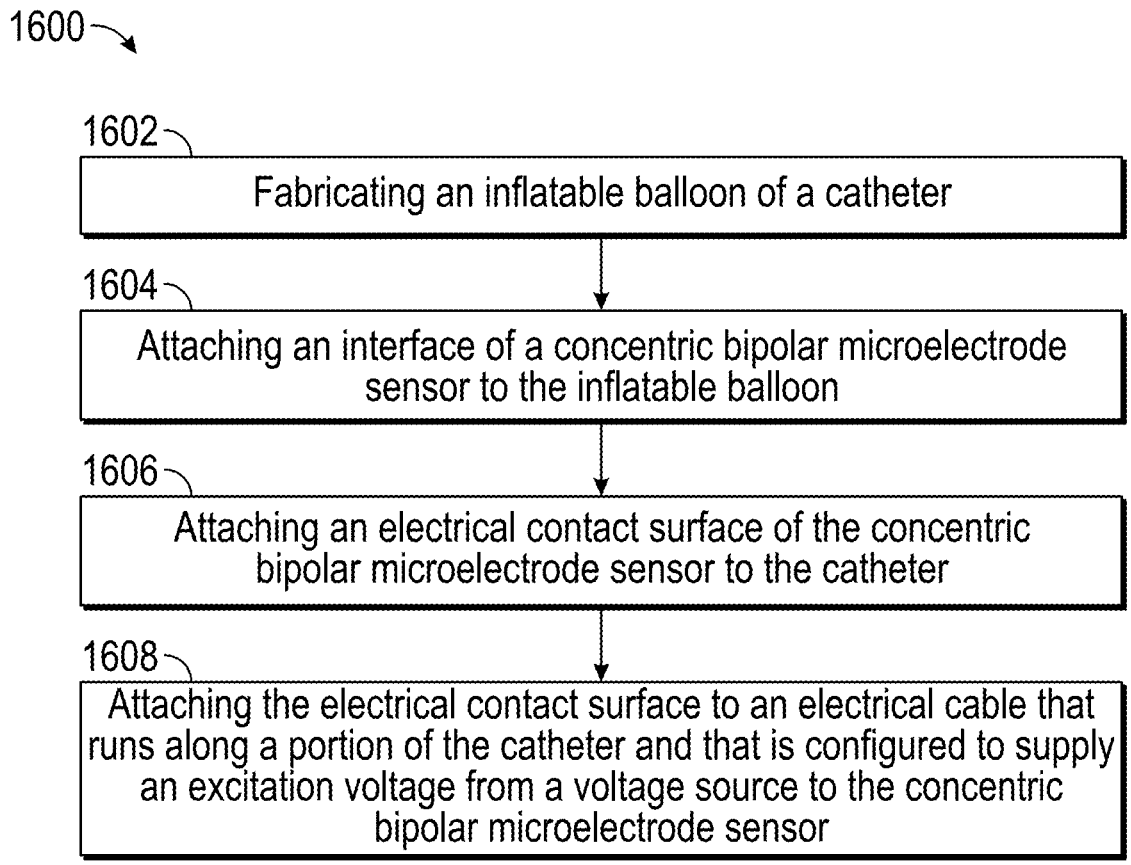
FIG. 16 illustrates an example manufacturing method of an electrical impedance apparatus, in accordance with an embodiment.

FIG. 16 illustrates another example method of manufacturing of an apparatus for EIS measurement. The apparatus includes a catheter having an inflatable balloon and an EIS sensor, where the EIS sensor is attached to the catheter. The example method of manufacturing includes multiple operations.

In an operation 1602, an inflatable balloon is fabricated. For instance, some or all of the fabrication steps of the example fabrication 1200 of FIG. 12 are performed to fabricate the inflatable balloon at a location (e.g., the tip) of the catheter.

In an operation 1604, the inflatable balloon is attached to the EIS sensor. For example, attachment pads of the EIS sensor are adhesively attached to an outer surface of the inflatable balloon. The attachment may be performed by following the example assembly 1400 of FIG. 14.

In an operation 1606, a portion of the catheter (e.g., an area of the body of the catheter) is attached to electrical contact surfaces of the EIS sensor. For example, the electrical contact surfaces of the EIS sensor are attached to the portion of the catheter. The attachment may be performed by following the example assembly 1400 of FIG. 14.

In an operation 1608, the electrical contact surfaces of the EIS sensor are connected to an electrical cable. The electrical cable runs along a portion of the catheter and is configured to supply an excitation voltage from a voltage source to the concentric bipolar microelectrodes of the EIS sensor. For example, the electrical cable includes a coaxial cable. Connecting the electrical cable may be performed by following the example assembly 1400 of FIG. 14.

Figure 17:
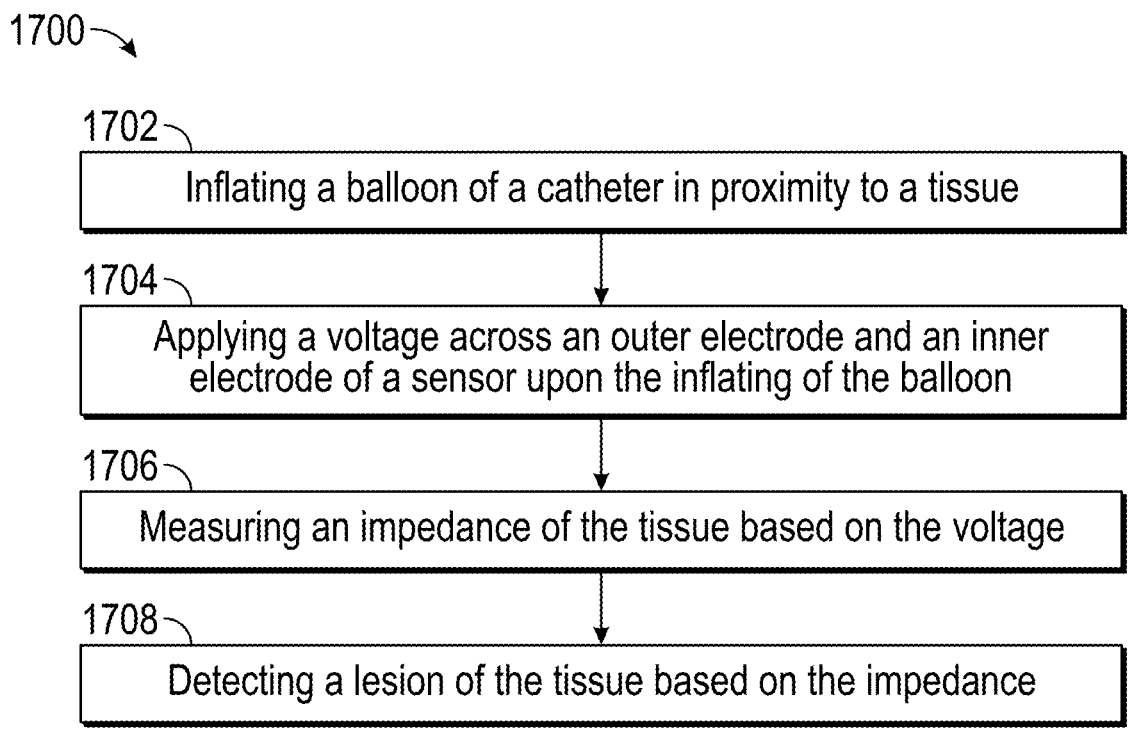
FIG. 17 illustrates a method of performing EIS measurement to diagnose a lesion, in accordance with an embodiment.

FIG. 17 illustrates a method of performing EIS measurement to diagnose a disease of a tissue, such as a lesion of the tissue. The EIS measurement uses an EIS sensor attached to a catheter that has an inflatable balloon. These components are part of an EIS diagnostic-based system. Such a system includes an impedance model that correlates impedances and diseases (e.g., lesions). The impedance model also provides instruction for choosing an inflatable balloon and an EIS sensor combination and for inflating the balloon to a certain inflation level based on a type and/or dimension of the tissue. The example method of FIG. 17 includes multiple operations.

In an operation 1702, the inflatable balloon of the catheter is inflated in proximity to a tissue. For example, the catheter is guided using fluoroscopy guidance such that the inflatable balloon is in close proximity to the tissue. The inflatable balloon is inflated to a certain inflation range. That inflation level increases the likelihood of contact between concentric biopolar microelectrodes of the EIS sensor and the tissue. The inflation range can be derived from the impedance model. In an example of an aorta of a certain dimension, the impedance model specifies that the inflatable balloon should be inflated to a pressure between five and nine psi (e.g., between 34,000 and 62,000 Pa), with seven psi (e.g., about 48,000 Pa) being the recommended level.

In an operation 1704, voltage across the concentric bipolar microelectrodes of the EIS sensor (e.g., the outer and inner electrodes) is applied upon the inflation of the inflatable balloon. The voltage is supplied through an electrical cable (e.g., a coaxial cable) to the EIS sensor from a voltage source. The voltage has a desired waveform across a frequency range (e.g., a range between 100 Hz and 100 kHz). The electrical cable is connected to electrical contact surfaces of the EIS sensor.

In an operation 1706, the impedance of the tissue is measured based on the applied voltage. For example, an impedance measuring device, such as a potentiostat, is connected to the electrical cable and measures the tissue's impedance.

In an operation 1708, a disease (e.g., a lesion) of the tissue is detected based on the impedance. For example, an analysis tool of the EIS diagnostic-based system compares the magnitude and/or phase of the measured impedance to a baseline impedance. The baseline impedance is stored at the impedance model or is developed by performing EIS measurements using the inflatable balloon in the deflated state and/or using known healthy tissue. In addition, the baseline impedance is developed for the same type and/or dimension of the tissue. Deviations between the measured and baseline impedance are detected. If the deviations exceed a threshold, the disease is diagnosed.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" includes within a tolerance of ±0.01%, ±0.1%, ±1%, ±2%, ±3%, ±4%, ±5%, ±8%, ±10%, ±15%, ±20%, ±25%, or as otherwise known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. An electrical impedance sensor comprising:
   an inner electrode disposed in a flat, circular ring;
   an outer electrode disposed in a flat, circular ring, wherein the outer electrode is concentric to the inner electrode and substantially surrounds the inner electrode, and wherein the outer electrode and the inner electrode form concentric electrodes;
   a first electrical contact surface;
   a pair of pads disposed on opposite sides of the concentric electrodes;
   a first ribbon cable extending radially from the inner electrode to a first pad of the pair of pads and further extending from the first pad to the first electrical contact surface; and
   a second ribbon cable extending radially from the outer electrode to a second pad of the pair of pads,
   wherein each of the first ribbon cable and the second ribbon cable is configured to extend and retract, and
   wherein a first portion of the first ribbon cable is between the inner electrode and the first pad and has a serpentine length.

2. The sensor of claim 1, wherein at least one ribbon cable of the ribbon cables has multiple serpentine lengths, at least one of the multiple serpentine lengths having a different wavelength than another wavelength of the multiple serpentine lengths of the at least one ribbon cable.

3. The sensor of claim 1, wherein the pair of pads is affixed to an outer surface of an inflatable balloon of a catheter.

4. The sensor of claim 3, wherein the inflatable balloon is located at an end of the catheter.

5. The sensor of claim 1, wherein the first electrical contact surface is connected to a first end of the first ribbon cable, and further comprising:
   a second electrical contact surface connected to a second end of the second ribbon cable,
   wherein the first electrical contact surface and the second electrical contact surface are affixed to a body of a catheter.

6. The sensor of claim 1, wherein the inner electrode has an inner diameter of about 75 μm.

7. The sensor of claim 1, wherein the outer electrode has a diameter of about 300 μm.

8. The sensor of claim 1, wherein the outer electrode, the inner electrode, a portion of the first ribbon cable, and a portion of the second ribbon cable are made of a same conductive material.

9. The sensor of claim 8, wherein the conductive material comprises at least one of: platinum or gold.

10. The sensor of claim 8, wherein first ribbon cable has a sinusoidal configuration.

11. The sensor of claim 8, wherein the first ribbon cable has a coiled configuration.

12. The sensor of claim 1, wherein the pair of pads, the first portion of the first ribbon cable, and a portion of the second ribbon cable are made of a same non-conductive material.

13. The sensor of claim 12, wherein the non-conductive material comprises parylene material.

14. The sensor of claim 1, wherein the first electrical contact surface is connected to a first end of the first ribbon cable, and further comprising:
   a second electrical contact surface connected to a second end of the second ribbon cable,
   wherein the first electrical contact surface and the second electrical contact surface are affixed to a catheter, wherein the first electrical contact surface is connected to a signal wire of a coaxial cable, wherein the second electrical contact is connected to a mesh ground wire of the coaxial cable, wherein the coaxial cable runs along a portion of the catheter and that supplies an excitation voltage to the concentric electrodes from a voltage source.

15. The sensor of claim 1, wherein the first electrical contact surface is connected to a first end of the first ribbon cable, and further comprising:
   a second electrical contact surface connected to a second end of the second ribbon cable,
   wherein the first electrical contact surface and the second electrical contact surface couple the sensor to a processor through an electrical cable, wherein the sensor and the processor belong to an electrical impedance spectroscopy (EIS) system.

16. The sensor of claim 15, wherein the concentric electrodes are affixed to an inflatable balloon of a catheter based on the pair of pads, and wherein the EIS measures impedance of a tissue based on the inflation of the inflatable balloon and an application of an excitation voltage to the tissue through the concentric electrodes, wherein the excitation voltage is applied upon the inflation of the inflatable balloon.

17. The electrical impedance sensor of claim 1, wherein a second portion of the first ribbon cable is between the first pad and the first electrical contact surface, wherein the second ribbon cable is separate from the first ribbon cable by being at a distance away from the first ribbon cable, and wherein the distance is larger than a diameter of the flat circular ring.

18. The electrical impedance sensor of claim 1, wherein the first pad is connected to or is a protruding part of the first ribbon cable.

19. An electrical impedance apparatus comprising:
a catheter comprising an inflatable balloon; and
an electrical impedance sensor comprising:
- an inner electrode disposed in a flat, circular ring;
- an outer electrode disposed in a flat, circular ring, the outer electrode concentric to the inner electrode and substantially surrounding the inner electrode;
- a first electrical contact surface;
- a pair of pads disposed on opposite sides of the concentric electrodes and attaching the outer electrode and the inner electrode to the inflatable balloon;
- a first ribbon cable extending radially from the inner electrode to a first pad of the pair of pads and further extending from the first pad to the first electrical contact surface; and
- a second ribbon cable extending radially from the outer electrode to a second pad of the pair of pads, wherein each of the first ribbon cable and the second ribbon cable is configured to extend and retract, and
wherein a first portion of the first ribbon cable is between the inner electrode and the first pad and has a serpentine length.

20. The apparatus of claim 19, wherein the inflatable balloon is configured to inflate between 34,000 Pa to 62,000 Pa, and wherein, upon an inflation of the balloon, the outer electrode and the inner electrode are configured to provide an excitation voltage with a frequency falling in a range between 100 Hz and 500 kHz.

* * * * *